(12) United States Patent
Chou et al.

(10) Patent No.: US 7,994,546 B2
(45) Date of Patent: Aug. 9, 2011

(54) METHOD FOR SODIUM ION SELECTIVE ELECTRODE, SODIUM ION SELECTIVE ELECTRODE THEREFROM AND SODIUM ION SENSING DEVICE

(75) Inventors: Jung-Chuan Chou, Yunlin County (TW); Ya-Ping Huang, Tainan (TW); Chien-Cheng Chen, Taichung County (TW)

(73) Assignee: National Yunlin University of Science and Technology, Yunlin (TW)

( * ) Notice: Subject to any disclaimer, the term of this patent is extended or adjusted under 35 U.S.C. 154(b) by 161 days.

(21) Appl. No.: 12/471,132

(22) Filed: May 22, 2009

(65) Prior Publication Data
US 2010/0207171 A1    Aug. 19, 2010

(30) Foreign Application Priority Data
Feb. 17, 2009  (TW) ............................. 98104928 A

(51) Int. Cl.
*G01N 27/403*    (2006.01)

(52) U.S. Cl. .......... 257/253; 257/222; 257/414; 257/40; 257/E51.027; 438/49; 204/630

(58) Field of Classification Search ................. 257/253, 257/222, 414, 40, E51.027; 204/630; 438/49
See application file for complete search history.

(56) References Cited

U.S. PATENT DOCUMENTS

| | | | |
|---|---|---|---|
| 2001/0032785 A1* | 10/2001 | Cha et al. ....................... | 204/435 |
| 2003/0209451 A1* | 11/2003 | Dineen et al. .................. | 205/789 |
| 2005/0040488 A1* | 2/2005 | Chou et al. ..................... | 257/428 |
| 2006/0011951 A1* | 1/2006 | Hsiung et al. .................. | 257/262 |
| 2006/0220092 A1* | 10/2006 | Chou et al. ..................... | 257/310 |

* cited by examiner

*Primary Examiner* — Tu-Tu V Ho

(57) ABSTRACT

The invention provides a method for forming a sodium ion selective electrode, including: (a) providing a conductive substrate; (b) forming a conductive wire which extends from the conductive substrate for external contact; and (c) forming a sodium ion sensing film on the conductive substrate, wherein the method for forming the conductive substrate includes: providing a substrate; and forming a conductive layer on the substrate.

40 Claims, 7 Drawing Sheets

METHOD FOR SODIUM ION SELECTIVE ELECTRODE, SODIUM ION SELECTIVE ELECTRODE THEREFROM AND SODIUM ION SENSING DEVICE

CROSS REFERENCE TO RELATED APPLICATIONS

This Application claims priority of Taiwan Patent Application No. 098104928, filed on Feb. 17, 2009, the entirety of which is incorporated by reference herein.

BACKGROUND OF THE INVENTION

1. Field of the Invention

The present invention relates to an ion selective electrode, and in particular relates to a sodium ion selective electrode.

2. Description of the Related Art

Conventionally, a polarography method and an atomic absorption spectrometry method were used to detect concentrations of potassium ions and sodium ions in blood. However, these methods require a pre-treatment, which makes the methods inconvenient to use. Ion sensitive field effect transistors (ISFET) having a silicon nitride ($Si_3N_4$) film is an improvement over metal insulating field effect transistors (MISFET) having a metal oxide film. For an ISFET, a silicon nitride ($Si_3N_4$) film with active substances is used as the ion sensing film and an Ag/AgCl is used as a reference electrode. Note that the ISFET sensor may be directly placed in a sample solution. When the substances in the sample solution reacts with receptors on the ion sensing film, a zeta potential of the ion sensing film is changed and a signal is acquired from drain of FET. An ISFET may be used to sense different kinds of ions by selecting different ion selective materials on the sensing film. Disclosed ISFETs can sense $Na^+$, $K^+$, $NH_4^+$, $Ca^{2+}$, $Ag^+$, $Li^+$, $Cl^-$ and $Br^-$, respectively.

Enzyme field effect transistors (EnFET) replace the ion sensing film of ISFETs with enzyme immobilized film. Conventionally, EnFETs were used for detecting penicillin, glucose or acetylcholine. The advantages of the ISFET comprise: (1) miniaturized size, which may be micro processed by a semiconductor technique; (2) multiplication, which allow processing as a sensor array to detect various compositions; (3) fast response, which reduces response time.

In 1983, J. Van der Spiegel et al. developed an extended gate chemical sensitive field effect transistor, which uses a plane array structure having four sensing parts deposited with different materials such as $IrO_x$, $LaF_3$, AgCl and $Ag_2S$ which form the sensing thin film for detecting four kinds of ions, $H^+$, $F^-$, $Cl^-$ and $Ag^+$.

Separative extended gate ion sensitive field effect transistors (SEGFET) are another kind of ISFET. Compared to conventional ISFETs, SEGFETs have advantages such as more simplified packaging, easier preservation, less light influence, less limitations on shape and size and better stability.

BRIEF SUMMARY OF THE INVENTION

The invention provides a method for forming a sodium ion selective electrode, comprising: (a) providing a conductive substrate; (b) forming a conductive wire which extends from the conductive substrate for external contact; and (c) forming a sodium ion sensing film on the conductive substrate.

The invention also provides a sodium ion selective electrode, comprising: (a) a conductive substrate; (b) a conductive wire which extends from the conductive substrate for external contact; and (c) a sodium ion sensing film on the conductive substrate.

The invention further provides a sodium ion sensing device, comprising: a metal-oxide-semiconductor field effect transistor; a semiconductor parameter analyzer coupled to a source and drain of the metal-oxide-semiconductor field effect transistor; the sodium ion selective electrode of the invention through the conductive wire coupled to a gate of the metal-oxide-semiconductor field effect transistor; and a reference electrode coupled to the semiconductor parameter analyzers, wherein the sodium ion selective electrode and the reference electrode dip into a sample solution to determine a concentration of the sample solution.

The invention further provides another sodium ion sensing device, comprising: the sodium ion selective electrode of the invention; a reference electrode; an instrumentation amplifier coupled to the sodium ion selective electrode and the reference electrode, and used to receive signals from the sodium ion selective electrode and the reference electrode; a digital meter coupled to the instrumentation amplifier to receive signals from the instrumentation amplifier; and a data recorder coupled to the digital meter to receive signals from the digital meter.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Each component constituting the sodium ion selective electrode of the invention will be described in greater detail. In this specification, expressions such as "overlying the substrate", "above the layer", or "on the film" simply denote a relative positional relationship with respect to the surface of the base layer, regardless of the existence of intermediate layers. Accordingly, the expressions may include not only the direct contact of layers, but also, non-contact state of one or more laminated layers.

Figure 1:
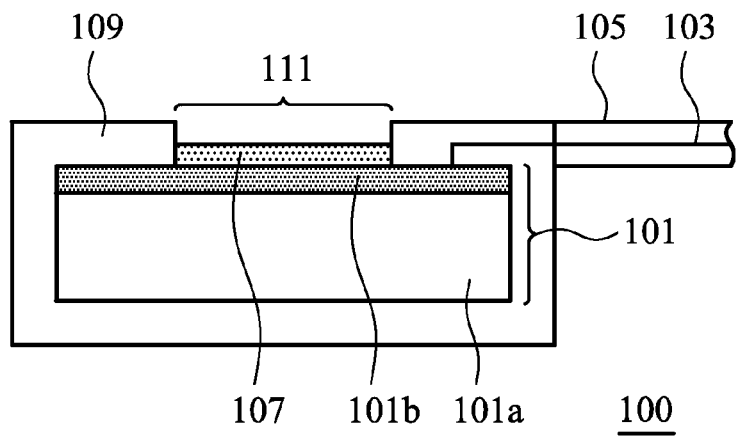
FIG. 1 shows a section view of a sodium ion selective electrode of one embodiment of the invention.
Figure 2:
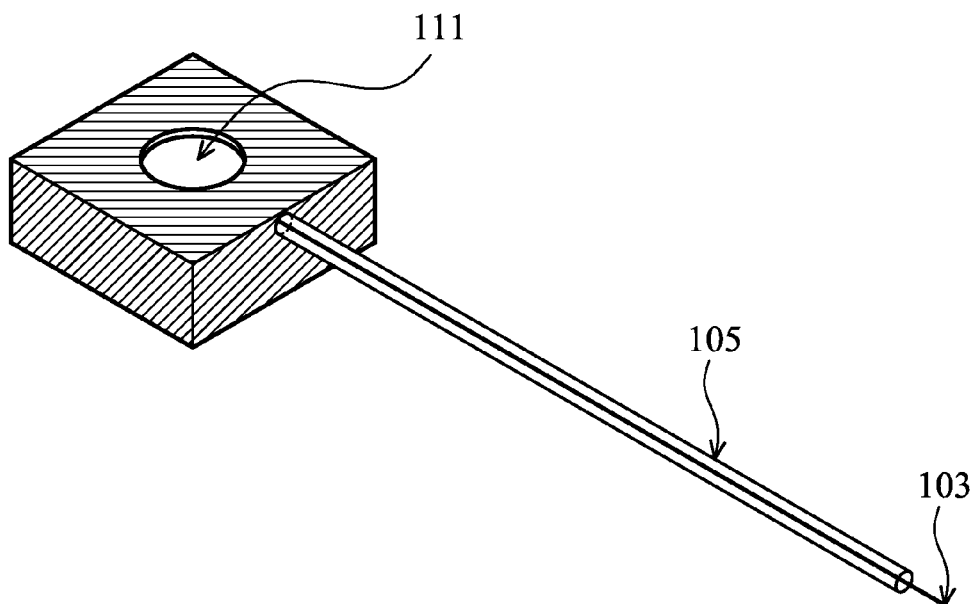
FIG. 2 shows an outside view of a sodium ion selective electrode of one embodiment of the invention.

Referring to FIGS. 1 and 2, FIG. 1 shows a section view of a sodium ion selective electrode of one embodiment of the invention and FIG. 2 shows an outside view of a sodium ion selective electrode of one embodiment of the invention. A method for forming a sodium ion selective electrode 100 of the invention is described in the following.

A conductive substrate 101 is provided. In one embodiment, the conductive substrate 101 may comprise a substrate having conductivity, such as indium tin oxide (ITO) glass. In another embodiment, a method for forming the conductive substrate 101 may comprise providing a substrate 101a and then forming a conductive layer 101b in the substrate 101a. A material of the substrate 101a may comprise silicon, screen printed plastic or glass, and a material of the conductive layer 101b may comprise ruthenium oxide or tin dioxide.

Then, a conductive wire 103 is extended from the conductive substrate 101 for external electric contact. The conductive wire 103 may be a metal wire, such as a copper wire. In one embodiment, a part of the conductive wire 103 is fixed on the conductive substrate 101 with sliver gel to make the conductive wire 103 extend from the conductive substrate 101 to the outside. Optionally, a mask 105 may be formed to cover the conductive wire 103, and the mask 105 may be a glass capillary.

Next, a sodium ion sensing film 107 is formed on the conductive substrate 101 to complete the sodium ion selective electrode of the invention 100. A processing material of the sodium ion sensing film 107 may comprise a polymeric material, a plasticizing agent, a sodium ion selective material and an anionic and sodium ion complex material. A weight ratio of the polymeric material, plasticizing agent, sodium ion selective material, and anionic and sodium ion complex material is about 33-44:66-88:3-4:5-15. In one embodiment, the processing material is added into a solvent to be thoroughly mixed to form a mixture and then the mixture is dropped on the conductive substrate 101 and after the solvent has evaporated, the sodium ion sensing film 107 is formed.

Moreover, the polymeric material may comprise polymer vinyl chloride (PVC), the plasticizing agent may comprise bis(2-ethylhe-xyl)sebacate (DOS), the sodium ion selective material may comprise Bis[(12-crown-4)methyl]-Dodecylmethylmalonate (B12C4), the anionic and sodium ion complex may comprise sodium tetrakis(4-fluorophenyl) borate dehydrate (Na-TFBD), and the solvent may comprise tetrahydrofuran (THF).

In another embodiment of the invention, after forming the conductive wire 103, an insulation layer 109 may be formed to package the conductive substrate 101, wherein the insulation layer 109 has a opening 111 exposing a part of a top surface of the conductive substrate 101, and the conductive wire 103 extends through the insulation layer 109 to the outside of the insulation layer 109. Then the sodium ion sensing film 107 is formed on a part of the top surface of the conductive substrate 101 exposed through the opening 111. A material of the insulation layer 109 may comprise epoxy resins. Optionally, after forming the insulation layer 109, a mask 105 may be formed to cover the conductive wire 103, and the mask 105 may be a glass capillary.

Figure 3:
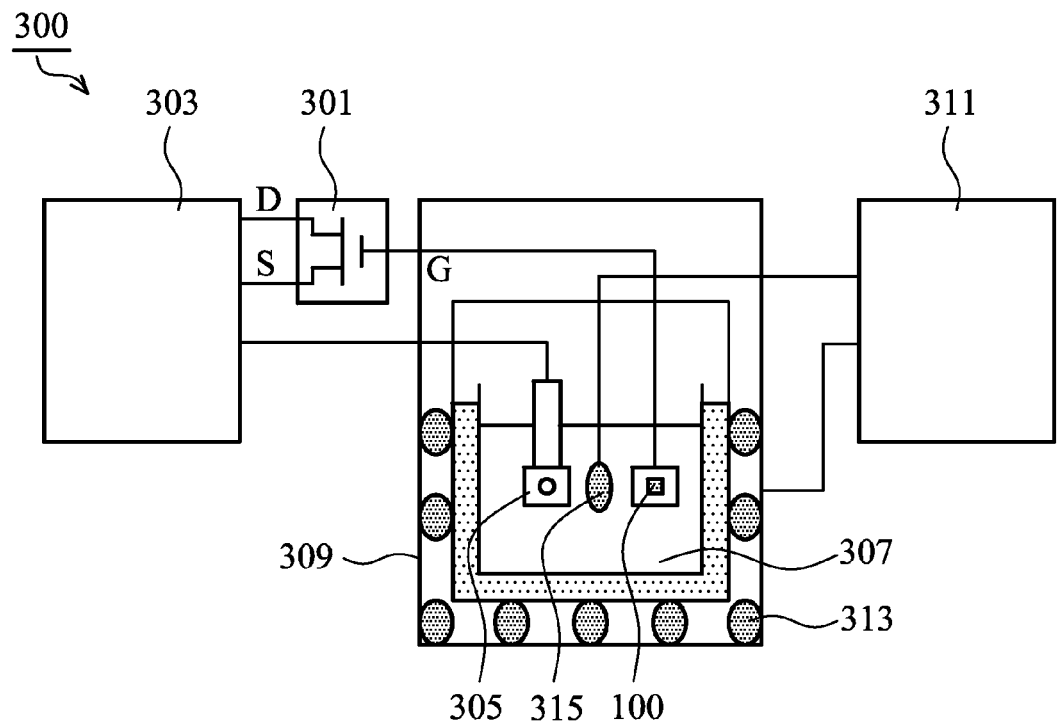
FIG. 3 shows a sodium ion sensing device of one embodiment of the invention (Current-Voltage (I-V) ion sensing device)

The sodium ion selective electrode 100 may combine with other devices to form a sodium ion sensing device. Referring FIG. 3, FIG. 3 shows a sodium ion sensing device of one embodiment of the invention (Current-Voltage (I-V) ion sensing device) 300. The sodium ion sensing device 300 may comprise a metal-oxide-semiconductor field effect transistor 301 which has a gate G, a source S and a drain D. A semiconductor parameter analyzer 303 may be coupled to the source S and drain D of the metal-oxide-semiconductor field effect transistor 301. Moreover, the sodium ion selective electrode 100 of the invention is coupled to the gate G of the metal-oxide-semiconductor field effect transistor 301 through the conductive wire 103. Furthermore, a reference electrode 305 may be coupled to the semiconductor parameter analyzer 303 to provide a stable potential. The sodium ion selective electrode and the reference electrode are dipped into a sample solution 307 to determine a sodium ion concentration of the sample solution 307. The reference electrode may comprise an Ag/AgCl reference electrode. The sodium ion sensing device 300 may further comprise a light isolated container 309 and a temperature controller 311. The temperature controller 311 may comprise a proportional-integral and derivative (PID) temperature controller. The light isolated container 309 is used for containing the sodium ion selective electrode 100, the reference electrode 305 and the sample solution 307, wherein the light isolated container 309 comprises at least one heater 313 coupled to the temperature controller 311 to control the temperature of the sample solution 307. Furthermore, a thermal coupler 315 coupled to the temperature controller 311 may additionally be configured in the sample solution 307 to stabilize the temperature of the sample solution 307.

Ion selective coefficients of potassium ions, calcium ions and magnesium ions to the sodium ion selective electrode calculated by a mach potential method are about $-1.95\sim1$, $-1.86\sim1$ and $-2\sim3.46$, respectively. Ion selective coefficients of potassium ions, calcium ions and magnesium ions to the sodium ion selective electrode calculated by a fixed interference method are about $-0.86\sim1$, $-1.52\sim1$ and $-1.38\sim3.46$, respectively. A sensitivity of the sodium ion selective electrode is about 56.11-61.97 mV/pNa when the sodium ion sensing device is in the sample solution at 25° C.-46° C.

Figure 4:
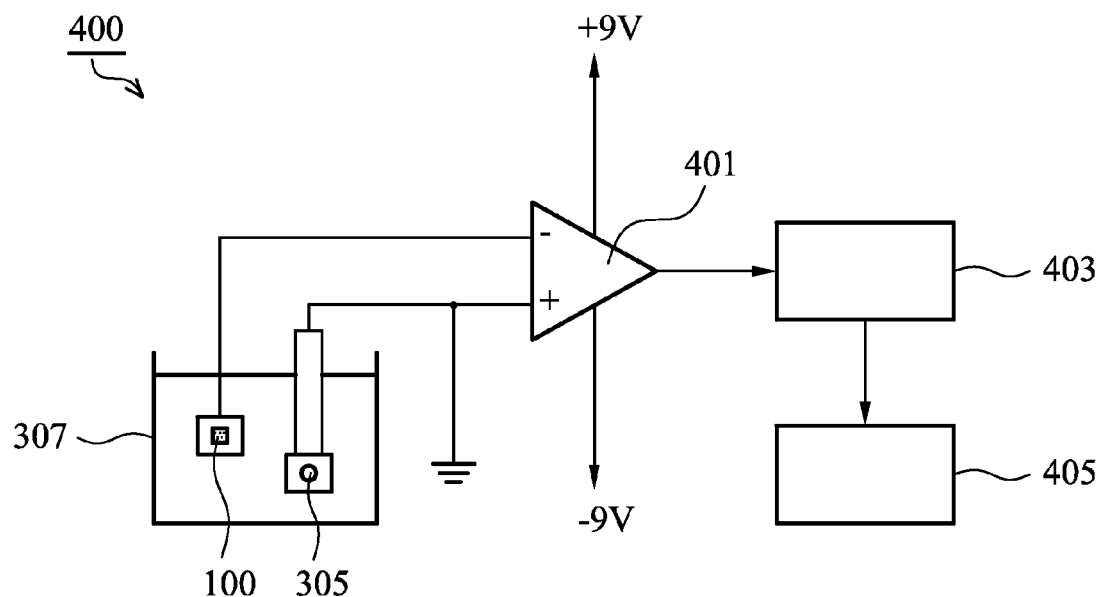
FIG. 4 shows a sodium ion sensing device of another embodiment of the invention (Voltage-Time (V-T) ion sensing device)

Referring FIG. 4, wherein FIG. 4 shows a sodium ion sensing device of another embodiment of the invention (Voltage-Time (V-T) ion sensing device) 400, the sodium ion sensing device 400 may comprise the sodium ion selective electrode 100 of the invention, a reference electrode 305, an instrumentation amplifier 401, a digital meter 403 and a data recorder 405. The instrumentation amplifier 401 is coupled to the sodium ion selective electrode 100 and the reference electrode 305 and is used to receive signals from the sodium ion selective electrode 100 and the reference electrode 305, wherein the sodium ion selective electrode 100 and the reference electrode 305 is dipped into the sample solution 307 to generate signals. Further, the digital meter 403 is coupled to the instrumentation amplifier 401 to receive signals from the instrumentation amplifier 401 and the data recorder 405 is coupled to the digital meter 403 to receive signals from the digital meter 403.

Compared to a conventional glass electrode, the miniaturized sodium ion selective electrode made of the polymer material of the invention has advantages of a smaller size, simpler processing, a lower cost, easier integration with disposable devices, and easier production. Thus, miniaturization and applicability for medical detection use is increased.

Furthermore, the sodium ion selective electrode of the invention is more easily integrated into a sensing chip, due to its stable sensing feature, for sensing of other ions.

Example

Preparation of the Sodium Ion Selective Electrode

1. Conductive Substrate

An indium tin oxide (ITO) glass substrate (Sinonar Corp. in Taiwan R.O.C) or a silicon substrate coated with ruthenium oxide was placed in an appropriate amount of acetone and oscillated by an ultrasonic cleaner for 5 minutes. Next, the conductive substrate was washed with D.I. water. Then, the conductive substrate washed by acetone was placed in an appropriate amount of acetone, oscillated by an ultrasonic cleaner for 5 minutes and then washed with D.I. water. After that, the conductive substrate was dried. A metal wire was fixed on the conductive substrate with silver gel and the device fixed with the metal wire was placed in an oven at 130° C. for 10 minutes. An epoxy resin was used to fix the silver gel part and package most of the device of the invention, leaving an opening with a size of 2 mm×2 mm and the device was placed in an oven at 130° C. for 10 minutes to dry the epoxy resin and exposed part of the conductive substrate. After drying, any small holes produced in the heated epoxy resin was refilled by the epoxy resin again and then baked at 130° C. to let the device packaged with epoxy resin can resist water in solution during usage.

2. Sodium Ion Sensing Film 0.33 g of PVC and 0.66 g of DOS were added into 5 ml of THF solution and then oscillated by an ultrasonic cleaner for 10 minutes to form a mixture solution. Then sodium ion selective material, B12C4 and anionic and sodium ion complex, and Na-TFBD were added into the mixture solution and then oscillated by an ultrasonic cleaner for 30 minutes to form a polymer solution, wherein the added mount of the Na-TFBD was 0.6 times that of the weight of the B12C4. Next, 2 ml of the polymer solution was dropped in the opening of the invention. After that, the device was placed for 8 hours and after drying the preparation of the sodium ion sensing film was completed. After the sodium ion sensing film was completed, the sodium ion selective electrode of the invention was completed.

Sodium Ion Sensing Device

1. Current-Voltage (I-V) Ion Sensing Device

The sodium ion selective electrode was electrically connected to a gate of a metal-oxide-semiconductor field effect transistor through a conductive wire and a source and drain of the metal-oxide-semiconductor were connected to a semiconductor parameter analyzer (Keithley 236, Keithley) through conductive wires, respectively. An Ag/AgCl reference electrode was placed in a sample solution to provide a stable potential and the Ag/AgCl reference electrode was coupled to the semiconductor parameter analyzer through a conductive wire. The sample solution, sodium ion selective electrode and reference electrode, etc. were placed into a light isolated container to prevent light from influencing the sensing process. In addition, in order to control the temperature of the buffer, the heaters were configured in the light isolated container, and were connected to a proportional-integral and derivative (PID) temperature controller. Furthermore, a thermal coupler was additionally configured in the sample solution and it was also connected to the proportional-integral and derivative (PID) temperature controller.

2. Voltage-Time (V-T) Ion Sensing Device

The sodium ion selective electrode of the invention was connected to an (−) input end of an instrumentation amplifier (LT1167) through a conductive wire. An Ag/AgCl reference electrode was connected to an (+) input end of the instrumentation amplifier through a conductive wire. An output voltage of the sodium ion selective electrode was transferred to a digital meter (HP 34401A) through the instrumentation amplifier. And the output voltage versus time curve was recorded by a data recorder.

Sensitivity Test for the Sodium Ion Selective Electrode

Figure 5:
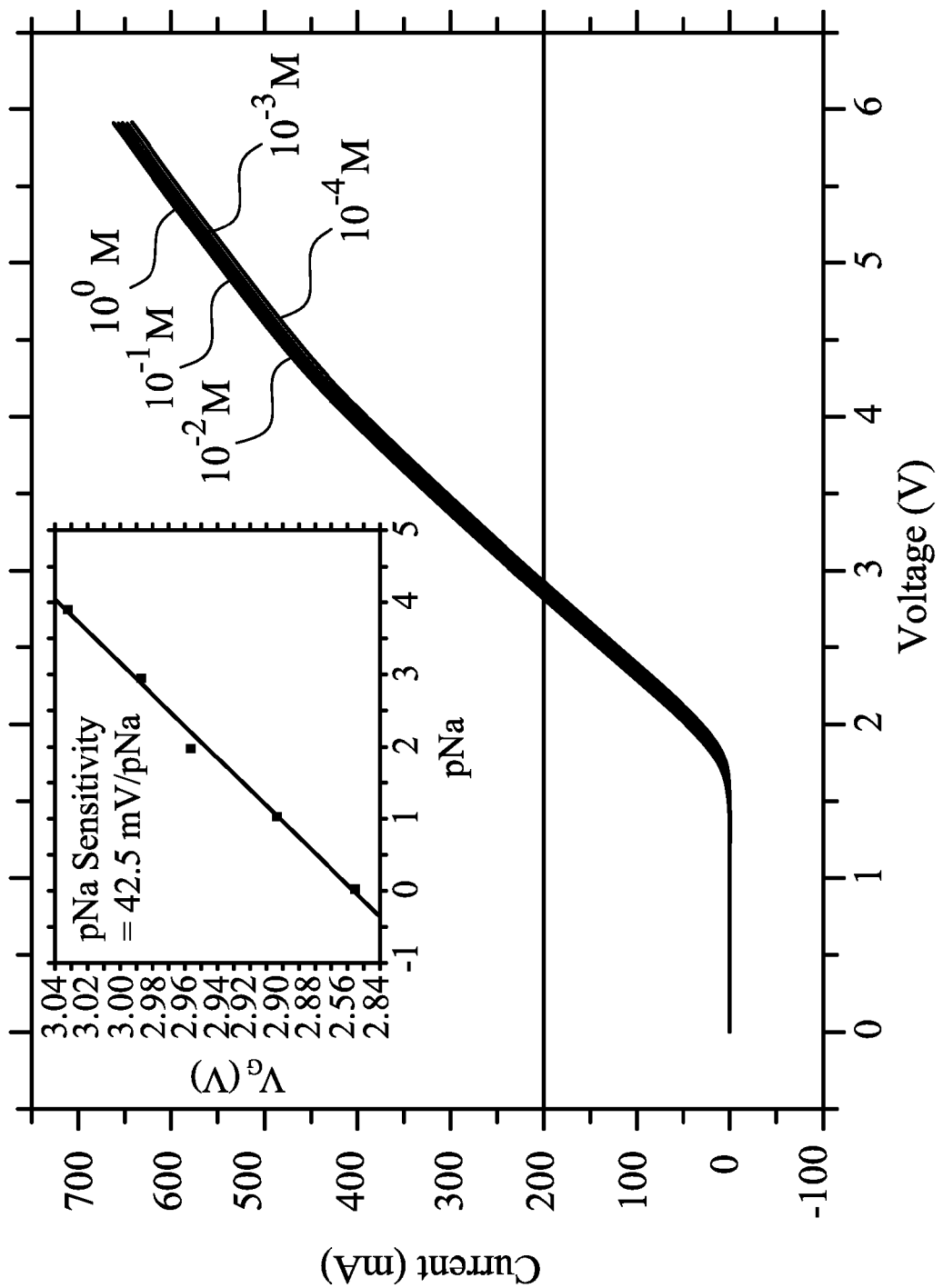
FIG. 5 shows the I-V curves and the sensitivity of the sodium ion selective electrode formed from an indium tin oxide (ITO) glass substrate.
Figure 6:
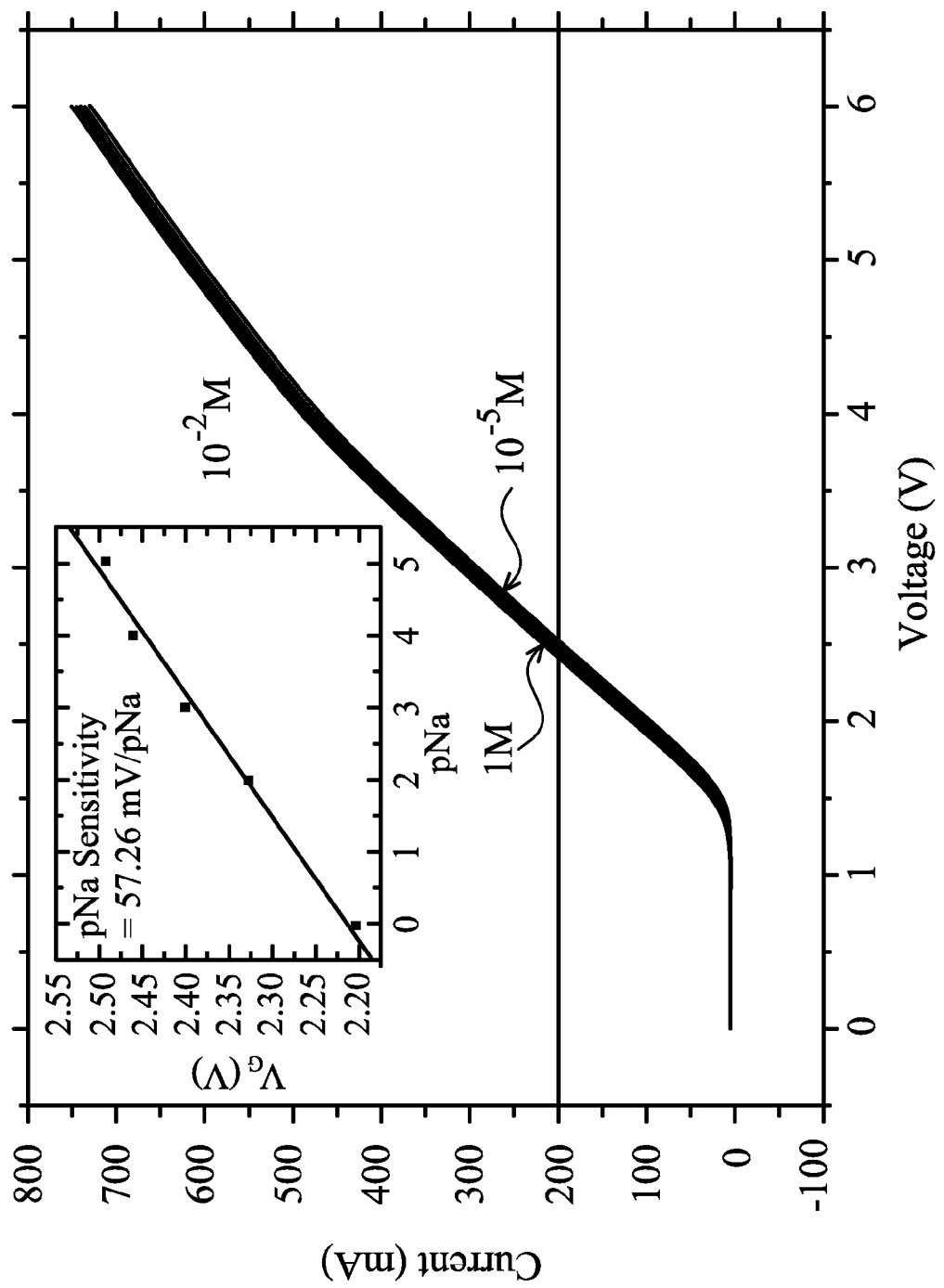
FIG. 6 shows the I-V curves and the sensitivity of the sodium ion selective electrode formed from a silicon substrate coated with ruthenium oxide.

The sensitivity tests were performed by the Current-Voltage (I-V) ion sensing device with the sodium ion selective electrode formed from an indium tin oxide (ITO) glass substrate and formed from a silicon substrate coated with ruthenium oxide by sodium ion sample solutions with different concentration, respectively. A commercial reference electrode (DX200) as a reference electrode was used for the sensitivity tests. The results are showed in FIG. 5 and FIG. 6, respectively. The results show that the sensitivity for the sodium ion selective electrode formed from an indium tin oxide (ITO) glass substrate was 42.5 mV/pNa, and the sensitivity for the sodium ion selective electrode formed from a silicon substrate coated with ruthenium oxide was 57.26 mV/pNa.

Response Time Test for the Sodium Ion Selective Electrode

Figure 7:
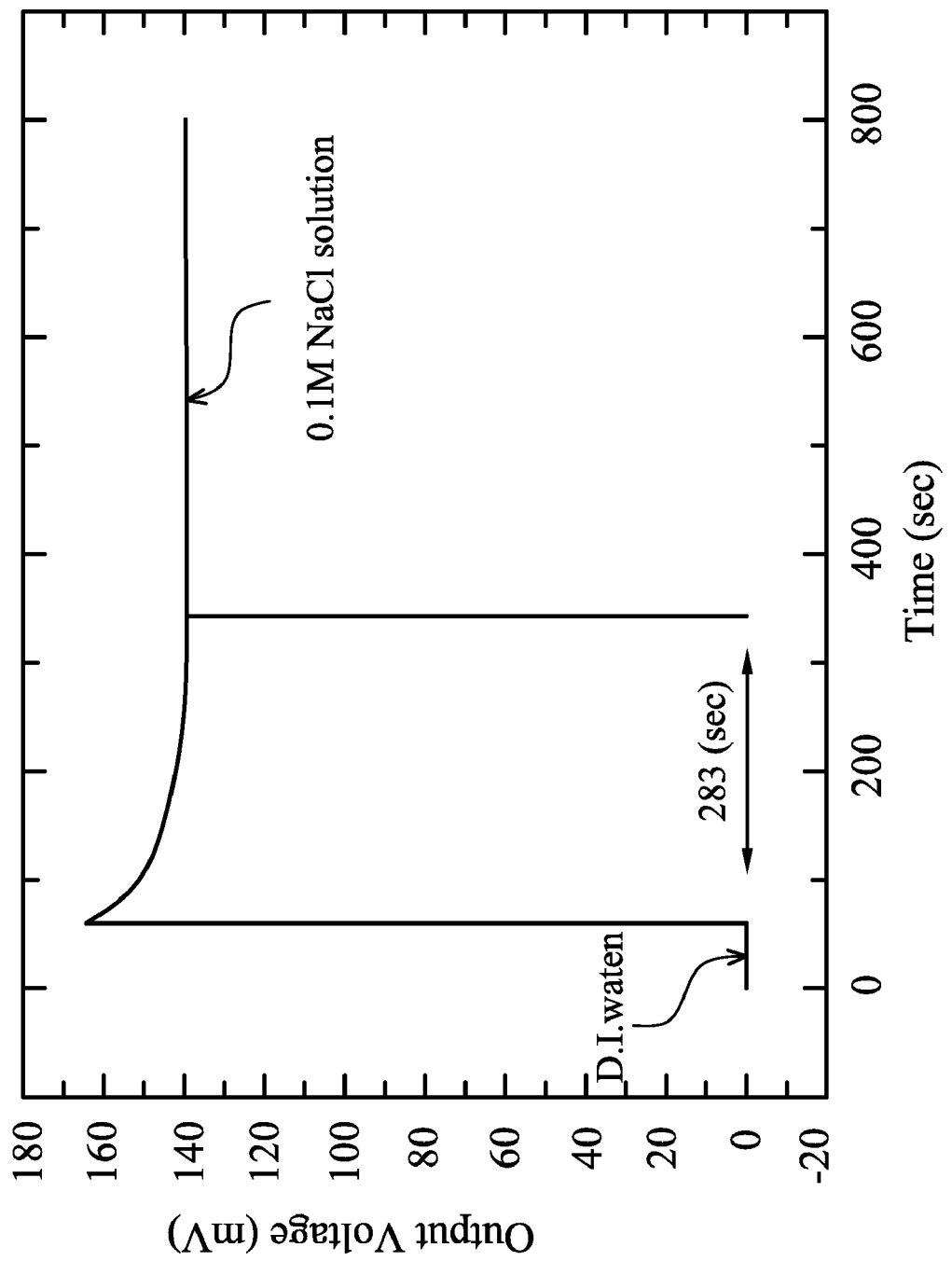
FIG. 7 shows the output voltage versus times that of the sodium ion selective electrode formed from an indium tin oxide (ITO) glass substrate in D.I. water and 0.1M NaCl solution.
Figure 8:
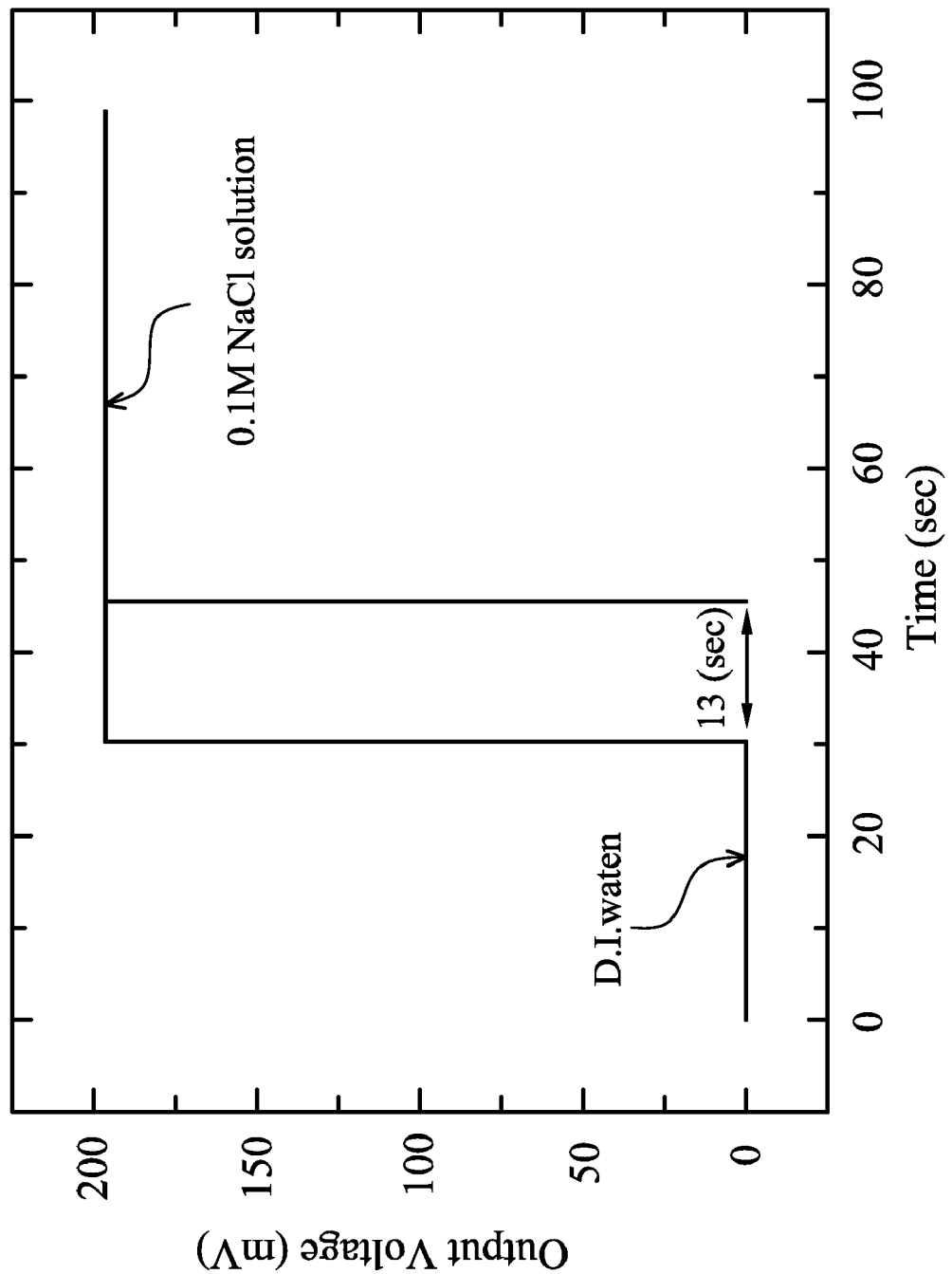
FIG. 8 shows the output voltage versus times that of the sodium ion selective electrode formed from a silicon substrate coated with ruthenium oxide in D.I. water and 0.1M NaCl solution.

The response time tests were performed by the Voltage-Time (V-T) ion sensing device with the sodium ion selective electrode formed from an indium tin oxide (ITO) glass substrate and formed from a silicon substrate coated with ruthenium oxide by 0.1 M sodium ion sample solution with different concentration, respectively. A commercial reference electrode (DX200) as a reference electrode was used fore the response time test. The results are showed in FIG. 7 and FIG. 8, respectively. The results show that the response time for the sodium ion selective electrode formed from an indium tin oxide (ITO) glass substrate was 283 seconds, and the response time for the sodium ion selective electrode formed from a silicon substrate coated with ruthenium oxide was 13 seconds.

Sensitivity Test for the Sodium Ion Selective Electrode for Different Temperatures The sensitivity tests were performed by the Current-Voltage (I-V) ion sensing device with the sodium ion selective electrode formed from a silicon substrate coated with ruthenium oxide by sodium ion sample solutions with different concentration at different temperatures, respectively. A commercial reference electrode (DX200) was used as a reference electrode. The results are showed in Table 1.

TABLE 1

Sensitivity of the sodium ion selective electrode at different temperatures

| Temperature (° C.) | Sensitivity (mV/pNa) | linearity |
|---|---|---|
| 26 | 57.14 | 0.990 |
| 36 | 61.97 | 0.991 |
| 46 | 56.11 | 0.996 |

The results show that between 26° C. and 46° C., the sodium ion selective electrode of the invention maintained a good linear sensitivity.

Ion Interference Calculation

The interference relationship of sodium ion and other ions may be obtained by an ion interference equation. In 1994, International Union of Pure and Applied Chemistry, IUPAC published that Nikolsky-Eisenman equation was an appropriate equation (1) for voltage electro-chemical sensor in an ion interference experiment. When the voltage interference parameter was fixed and the concentration of the interfering ions was known, the real value of the concentration of the principal ions was obtained by the following equation:

$$E = \text{constant} + \frac{2.303RT}{Z_A F} \log \left[ a_A + K_{A,B}^{pot} a_B^{Z_A/Z_B} + K_{A,C}^{pot} a_C^{Z_A/Z_B} + \ldots \right] \quad (1)$$

wherein $a_A$ was the concentration of principal ion A, $a_B$, $a_C$ ... were the concentrations of the interfering ions, $K_{A,B}^{pot}$ was the potentiometric selectivity coefficient for ion B with respect to the principal ion A, $Z_A$ was the charge number corresponding to the charge of the principal ion A, and $Z_B$ and $Z_C$ were charge numbers corresponding to the charge of interfering ions B, C, . . . , respectively.

The $K_{A,B}^{pot}$ parameter, assumes that an ion selective electrode may be used to distinguish other ions or other compositions. The parameter may be obtained through response voltages for a principal ion A and interfering ions B of an ion selective electrode in a mixture. The smaller the parameter is, the more responsive the voltage of the device is to the principal ion A. For example, when a sodium ion selective electrode is used, the smaller the parameter is, the more responsive the voltage of the device is to the sodium ion. Meanwhile, the smaller the determined selectivity coefficient is, lower the influence on the potential from an interfering substance. Therefore, the smaller the determined selectivity coefficient is, the better the selective ability of an ion selective electrode for target A is.

There are four methods for determining $K_{A,B}^{pot}$ which include the separate solution method (SSM), separate solution method II (SSM II), fixed interference method (FIM) and matched potential method (MPM). The fixed interference method (FIM) and matched potential method (MPM) were used in the examples of the invention. The two methods are described in the following.

(1) Fixed Interference Method

Figure 9:
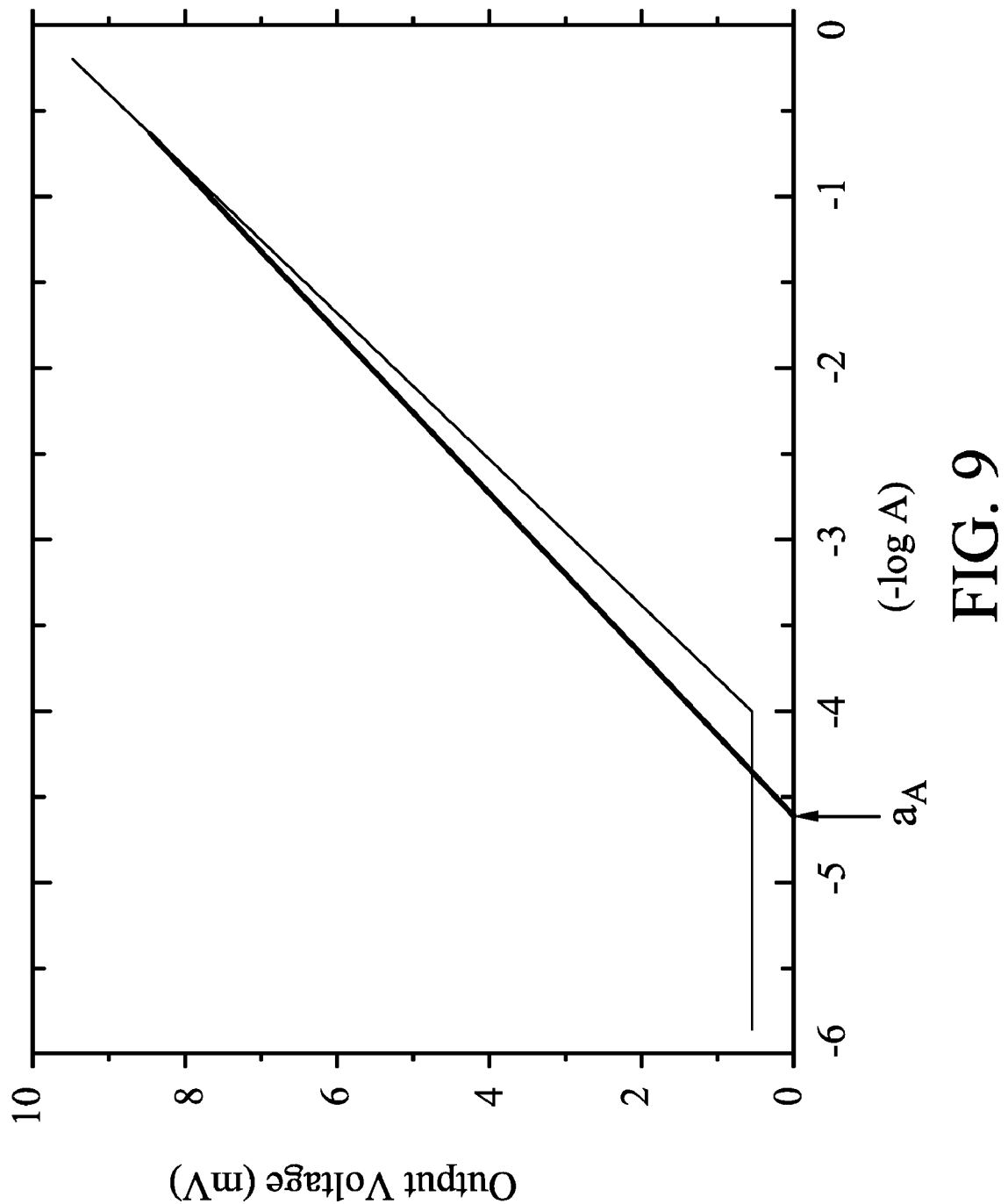
FIG. 9 shows the principle of the determination of selectivity coefficients $a_A$ by the matched potential method (MPM).

A concentration of interfering ions was fixed and a concentration of a principal ion was changed (determined by the log change of the concentration). $Z_A$ was the charge number corresponding to the charge of the principal ion A, and $Z_B$ was the charge number corresponding to the charge of interfering ions B. The value of $a_A$ was the value of the concentration of the principal ion on the X axis crossed by the tangent line of linearity, as shown in FIG. 9. The selectivity coefficient was obtained from equation (2) as follows:

$$K_{AB}^{pot} = \frac{a_A}{a_B^{Z_A/Z_B}}. \quad (2)$$

(2) Matched Potential Method

The response curve of the principal ion A was determined first, then the concentration of the principal ion was fixed and an interfering ion was added to determine the response curve. Next, the selectivity coefficient was obtained from equation (3) and (4) as follows:

$$\Delta a_A = a'_A - a_A \quad (3); \text{ and}$$

$$K_{A,B}^{pot} = \Delta a_A / a_B \quad (4).$$

The Voltage-Time (V-T) ion sensing device with the sodium ion selective electrode formed from a silicon substrate coated with ruthenium was applied to potassium ions, calcium ions and magnesium ion solutions to perform tests. A commercial reference electrode (DX200) was used as a reference electrode. The results are showed in Table 2.

TABLE 2

Determination of the selectivity coefficient

| Principal ion (A) Na$^+$ interfering ion (B) | Fixed interference method (FIM) log $K_{A,B}^{Pot}$ | Match potential method (MPM) log $K_{A,B}^{Pot}$ |
|---|---|---|
| calcium ion Ca$^{2+}$ | −0.86 | −1.86 |
| potassium ion K$^+$ | −1.52 | −1.95 |
| magnesium ion Mg$^{2+}$ | −1.38 | −3.46 |

The results show that the selective coefficients of potassium ions, calcium ions and magnesium ions of the selective electrode from the invention calculated by the mach potential method were −1.95, −1.86 and −3.46, respectively. The results show that the selective coefficients of the potassium ions, calcium ions and magnesium ions of the selective electrode from the invention calculated by the fixed interference method were −0.86, −1.52 and −1.38, respectively.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method for forming a sodium ion selective electrode, comprising:
    (a) providing a conductive substrate;
    (b) forming a conductive wire which extends from the conductive substrate for external contact; and
    (c) forming a sodium ion sensing film on the conductive substrate,
    wherein the processing material for forming the sodium ion sensing film comprises a polymeric material, a plasticizing agent, a sodium ion selective material and an anionic and sodium ion complex material.

2. The method for forming a sodium ion selective electrode as claimed in claim 1, wherein the method for forming the conductive substrate comprises:
    providing a substrate; and
    forming a conductive layer on the substrate.

3. The method for forming a sodium ion selective electrode as claimed in claim 2, wherein the material of the substrate comprises silicon, screen printed plastic or glass.

4. The method for forming a sodium ion selective electrode as claimed in claim 2, wherein the conductive layer comprises ruthenium oxide or tin dioxide.

5. The method for forming a sodium ion selective electrode as claimed in claim 1, wherein the conductive substrate comprises indium tin oxide (ITO) glass.

6. The method for forming a sodium ion selective electrode as claimed in claim 1, wherein the processing material is added into a solvent.

7. The method for forming a sodium ion selective electrode as claimed in claim 1, wherein a weight ratio of the polymeric material, plasticizing agent, sodium ion selective material, and anionic and sodium ion complex material is about 33-44: 66-88:3-4:5-15.

8. The method for forming a sodium ion selective electrode as claimed in claim 1, wherein the polymeric material comprises polymer vinyl chloride (PVC).

9. The method for forming a sodium ion selective electrode as claimed in claim 1, wherein the plasticizing agent comprises bis(2-ethylhe-xyl)sebacate (DOS).

10. The method for forming a sodium ion selective electrode as claimed in claim 1, wherein the sodium ion selective material comprises Bis[(12-crown-4)methyl]-Dodecylmethylmalonate (B12C4).

11. The method for forming a sodium ion selective electrode as claimed in claim 1, wherein the anionic and sodium ion complex comprises sodium tetrakis(4-fluorophenyl) borate dehydrate (Na-TFBD).

12. The method for forming a sodium ion selective electrode as claimed in claim 6, wherein the solvent comprises tetrahydrofuran.

13. The method for forming a sodium ion selective electrode as claimed in claim 6, further comprising between step (b) and step (c), forming an insulation layer to package the conductive substrate, wherein the insulation layer has an opening exposing a part of a top surface of the conductive substrate, and the conductive wire extends through the insulation layer to the outside of the insulation layer.

14. The method for forming a sodium ion selective electrode as claimed in claim 13, wherein a material of the insulation layer comprises epoxy resins.

15. The method for forming a sodium ion selective electrode as claimed in claim 1, further comprising after the step (b), forming a mask to cover the conductive wire.

16. The method for forming a sodium ion selective electrode as claimed in claim 13, further comprising after forming the insulation layer, forming a mask to cover a part of the conductive wire that is extending to the outside of the insulation layer.

17. A sodium ion selective electrode, comprising:
(a) a conductive substrate;
(b) a conductive wire which extends from the conductive substrate for external contact; and
(c) a sodium ion sensing film on the conductive substrate, wherein a processing material for forming the sodium ion sensing film comprises a polymeric material, a plasticizing agent, a sodium ion selective material and an anionic and sodium ion complex material.

18. The sodium ion selective electrode as claimed in claim 17, wherein the conductive substrate comprises:
a substrate; and
a conductive layer on the substrate.

19. The sodium ion selective electrode as claimed in claim 18, wherein a material of the substrate comprises silicon, screen printed plastic or glass.

20. The sodium ion selective electrode as claimed in claim 18, wherein the conductive layer comprises ruthenium oxide or tin dioxide.

21. The sodium ion selective electrode as claimed in claim 17, wherein the conductive substrate comprises indium tin oxide (ITO) glass.

22. The sodium ion selective electrode as claimed in claim 17, wherein the processing material is added into a solvent.

23. The sodium ion selective electrode as claimed in claim 17, wherein a weight ratio of the polymeric material, plasticizing agent, sodium ion selective material, and anionic and sodium ion complex material is about 33-44:66-88:3-4:5-15.

24. The sodium ion selective electrode as claimed in claim 17, wherein the polymeric material comprises polymer vinyl chloride (PVC).

25. The sodium ion selective electrode as claimed in claim 17, wherein the plasticizing agent comprises bis(2-ethylhe-xyl)sebacate (DOS).

26. The sodium ion selective electrode as claimed in claim 17, wherein the sodium ion selective material comprises Bis[(12-crown-4)methyl]-Dodecylmethylmalonate (B12C4).

27. The sodium ion selective electrode as claimed in claim 17, wherein the anionic and sodium ion complex comprises sodium tetrakis(4-fluorophenyl) borate dehydrate (Na-TFBD).

28. The sodium ion selective electrode as claimed in claim 22, wherein the solvent comprises tetrahydrofuran.

29. The sodium ion selective electrode as claimed in claim 17, further comprising an insulation layer to package the conductive substrate, wherein the insulation layer has an opening exposing a part of a top surface of the conductive substrate, and the conductive wire extends through the insulation layer to the outside of the insulation layer.

30. The sodium ion selective electrode as claimed in claim 29, wherein a material of the insulation layer comprises epoxy resins.

31. The sodium ion selective electrode as claimed in claim 17, further comprising a mask to cover the conductive wire.

32. The sodium ion selective electrode as claimed in claim 29, further comprising a mask covering a part of the conductive wire that is extending to the outside of the insulation layer.

33. A sodium ion sensing device, comprising:
a metal-oxide-semiconductor field effect transistor;
a semiconductor parameter analyzer coupled to a source and drain of the metal-oxide-semiconductor field effect transistor;
the sodium ion selective electrode as claimed in claim 17 through the conductive wire coupled to a gate of the metal-oxide-semiconductor field effect transistor; and
a reference electrode coupled to the semiconductor parameter analyzers, wherein the sodium ion selective electrode and the reference electrode are dipped into a sample solution to determine a sodium ion concentration of the sample solution.

34. The sodium ion sensing device as claimed in claim 33, further comprising:
a light isolated container for containing the sodium ion selective electrode, the reference electrode and the sample solution, wherein the light isolated container comprises at least one heater; and
a temperature controller coupled to the heater.

35. The sodium ion sensing device as claimed in claim 34, wherein the temperature controller comprises the proportional-integral and derivative (PID) temperature controller.

36. The sodium ion sensing device as claimed in claim 33, wherein ion selective coefficients of potassium ions, calcium ions and magnesium ions to the sodium ion selective electrode calculated by a mach potential method are about −1.95~1, −1.86~1 and −2~3.46, respectively.

37. The sodium ion sensing device as claimed in claim 33, wherein ion selective coefficients of potassium ions, calcium ions and magnesium ions to the sodium ion selective electrode calculated by a fixed interference method are about −0.86~1, −1.52~1 and −1.38~3.46, respectively.

38. The sodium ion sensing device as claimed in claim 33, wherein a sensitivity of the sodium ion selective electrode is about 56.11-61.97 mV/pNa when the sodium ion sensing device is in the sample solution at 25° C.-46° C.

39. A sodium ion sensing device, comprising:

the sodium ion selective electrode as claimed in claim 17;

a reference electrode;

an instrumentation amplifier coupled to the sodium ion selective electrode and the reference electrode, and used to receive signals from the sodium ion selective electrode and the reference electrode;

a digital meter coupled to the instrumentation amplifier to receive signals from the instrumentation amplifier; and a data recorder coupled to the digital meter to receive signals from the digital meter.

40. The sodium ion sensing device as claimed in claim 39, wherein the reference electrode comprises an Ag/AgCl reference electrode.

* * * * *